(12) United States Patent
Cagnac et al.

(10) Patent No.: US 12,031,120 B2
(45) Date of Patent: *Jul. 9, 2024

(54) METHOD FOR CULTURING UNICELLULAR RED ALGAE (URA) WITH MILK PERMEATE

(71) Applicant: FERMENTALG, Libourne (FR)

(72) Inventors: Olivier Cagnac, Libourne (FR); Bruno Gehin, Saint Emilion (FR); Marion Champeaud, Langoiran (FR)

(73) Assignee: FERMENTALG, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/734,621

(22) Filed: May 2, 2022

(65) Prior Publication Data

US 2022/0372428 A1 Nov. 24, 2022

Related U.S. Application Data

(63) Continuation of application No. 15/780,714, filed as application No. PCT/EP2016/079325 on Nov. 30, 2016, now Pat. No. 11,365,387.

(30) Foreign Application Priority Data

Dec. 4, 2015 (FR) ...................................... 1561839

(51) Int. Cl.
*C12N 1/12* (2006.01)
*A23K 10/16* (2016.01)

(52) U.S. Cl.
CPC ................ *C12N 1/12* (2013.01); *A23K 10/16* (2016.05)

(58) Field of Classification Search
None
See application file for complete search history.

(56) References Cited

U.S. PATENT DOCUMENTS

| | | | | |
|---|---|---|---|---|
| 11,365,387 | B2 * | 6/2022 | Cagnac | .................... C12N 1/12 |
| 2012/0128851 | A1 * | 5/2012 | Brooks | ................. A23K 10/16 |
| | | | | 426/549 |

FOREIGN PATENT DOCUMENTS

| | | |
|---|---|---|
| EP | 2730647 A1 | 3/2017 |
| FR | 3041653 A1 | 8/1996 |
| FR | 2789399 A1 | 8/2000 |
| WO | 2011/035166 A1 | 3/2011 |
| WO | 2012/035262 A1 | 3/2012 |
| WO | 2012/175866 A1 | 12/2012 |
| WO | 2014/074769 A1 | 5/2014 |
| WO | 2014/174182 A1 | 10/2014 |
| WO | 2016/030629 A1 | 3/2016 |
| WO | 2016/099261 A1 | 6/2016 |

OTHER PUBLICATIONS

Tischendorf et al. Eur. J. Phycol., 2007, 42(3), pp. 243-251.*
Bumback et al. Appl Microbiol Biotechnology, 2001, 91, pp. 31-46.*
Sloth et al. "Accumulation of Phycocyanin in heterotrophic and mixotrophic cultures of the acidophilic red alga *Saldieria sulphuraria*", Enzy and Microbial Technologie, 2006, vol. 38, pp. 168-175.
Graverholt et al. "Heterotrophic high-cell-density fed-batch and continuous-flow cultures of Galdieria sulphuraria and production of phycocyanin", Appl. Microbiol Biotechnol, 2007, vol. 77, pp. 69-75.
Steinmuller et al. "Photo- and Metabolite Regulation of the Sysnthesis of Ribulose Bisphosphate Carboxylase/Oxygenase and the Phycobiliproteins in the Alga *Cyanidium caldarium*"; Plant Physiol., 1984, vol. 76, pp. 935-939.
Niichols et al. "Action Spectra Studies of Phycocyanin Formation in a Mutant of Cyanidium Caldarium", Botanical Gazette, Dec. 1962, pp. 85-93.
Schulze et al. "Light emitting diodes (LEDs) applied to Microalgal production", Trends in Biotechnology, Aug. 2014, vol. 32, No. 8, pp. 422-430.
Kao et al. "Physical-Chemical Properties of C-Phycocyanin Isolated from an Acido-Thermophilic Eukaryote, Cyanidium caldarium", Biochem. J., 1975, vol. 147, pp. 63-70.
Eisele et al. "Studies on C-phycocyanin from Cyanidium caldarium, a eukaryote at the extremes of habitat", Biochimica et Biophysica Acta 1456, 2000, pp. 99-107.
Moon et al. "Isolation and characterization of thermostable phycocyanin from Galdieria sulphuraria", Korean J. Chem. Eng., 2014, vol. 31, No. 3, pp. 490-495.
Rahman et al. "Thermostable phycocyanin from the red microalga *Cyanidioschyzon merolae*, a new natural blue food colorant", J. Appl. Phycol., Nov. 2016.
Tischendorf et al. "Ultrastructure and enzyme complement of proplastids from heterotrophically grown cells of the red alga *Galdieria sulphuraria*", European Journal of Phycology, 2007, vol. 42, No. 3, pp. 243-251.
Gross et al. "Heterotrophic Growth of Two Strains of the Acido-Thermophilic Red Alga *Galdieria sulphuraria*", Plant and Cell Physiology, 1995, vol. 36, No. 4, pp. 633-638.
Bumbak et al. "Best practices in heterotrophic high-cell-density microalgal processes: achievements, potential and possible limitations", Appl Microbiol Biotechnol, 2011, vol. 91, pp. 31-46.
Schmidt et al. "Heterotrophic high cell-density fed-batch cultures of the phycocyanin-producing red alga *Galdieria sulphuraria*", Biotechnology and Bioengineering, Apr. 5, 2005, vol. 90, No. 1, pp. 77-84.
Barbier et al. "Comparative genomics of two closely related unicellular thermo-acidophilic red algae, *Galdieria sulphuraria* and *Cyanidioschyzon merolae*, reveals the molecular basis of the metabolic flexibility of Galdieria sulphuraria and significant differences in carbohydrate metabolism of both algae", Plant Physiology, Feb. 2005, vol. 137, pp. 460-474.

(Continued)

*Primary Examiner* — Vera Afremova

(74) *Attorney, Agent, or Firm* — BCF LLP

(57) ABSTRACT

The present invention relates to the field of culturing unicellular red algae (URA). The invention relates in particular to a method for culturing URA, characterised in that the culture medium includes milk permeate as the main contribution of at least one carbon source. The invention also relates to biomass which can be obtained by the method according to the invention, to the uses of said biomass and to the products that can include said biomass.

16 Claims, 3 Drawing Sheets

(56) References Cited

OTHER PUBLICATIONS

Henkanatte-Gedera et al. "Algal-based, single-step treatment of urban wastewaters", Bioresource Technology, 2015, vol. 189, pp. 273-278.

Chen et al. "High cell density mixotrophic culture of Spirulina platensis on glucose for phycocyanin production using a fed-batch system", Enzyme Microb. Technol., Feb. 15, 1997, vol. 20, pp. 221-224.

Jaouen et al. "Clarification and concentration with membrane technology of a phycocyanin solution extracted from Spirulina platensis", Biotechnology Techniques, 1999, vol. 13, pp. 877-881.

Rellan et al. "First detection of anatoxin-a in human and animal dietary supplements containing cyanobacteria", Food and Chemical Toxicology, 2009, vol. 47, pp. 2189, 2195.

Patrickios et al. "Polypeptide Amino Acid Composition and Isoelectric Point II. Comparison between Experiment and Theory", Analytical Biochemistry, 1995, vol. 231, pp. 82-91.

Linablue® Natural blue colorant derived from DIC Spirulina. [online]. "Vital Spiral" Spirulina, DIC Lifetec Co. Ltd., retrieved on May 10, 2018; Retrieved from the Internet: <URL: http://www.dlt-spl.ca.jp/business/en/spirulina/linablue.html.

Stadnichuk et al. "Inhibition by glucose of chlorophyll a and phycocyanobilin biosynthesis in the unicellular red alga *Galdieria partita* at the stage of coproporphyrinogen III formation", Plant Science, 1998, vol. 136, pp. 11-23.

Nichols et al. "Studies an Phycobilin Formation with Mutants of Cyanidium caldarium", Nature, 1960, vol. 188, pp. 870-872.

Borges et al., Bio-oil production and removal of organic load by microalga *Scenedesmus* sp. using culture medium contaminated with different sugars, cheese whey and whey permeate, Journal of Environmental Management 173 ; 2016, 134-140.

Abreu et al., Mixotrophic cultivation of Chlorella vulgaris using industrial dairy waste as organic carbon source, Bioresource Technology 118 (2012) 61-66.

Albertano et al., "The taxonomic position of Cyanidium, Cyanidioschyzon and Galdieria: an update". Hydrobiologia.2000, 433, pp. 137-143.

\* cited by examiner

METHOD FOR CULTURING UNICELLULAR RED ALGAE (URA) WITH MILK PERMEATE

CROSS-REFERENCE TO RELATED APPLICATIONS

This U.S. Patent Application is a Continuation Application of U.S. patent application Ser. No. 15/780,714, filed on Jun. 1, 2018, which is a U.S. National Stage Patent Application of International Application No. PCT/EP2016/079325 filed on Nov. 30, 2016, which claims priority from French Patent Application No. 1561839 filed Dec. 4, 2015, the content of all of which is herein incorporated in its entirety by reference.

FIELD OF THE INVENTION

The present invention relates to the field of culturing unicellular red algae (URA). The invention particularly relates to a method for culturing URA, characterized in that the culture medium includes lacteal permeate as principal supply of at least one carbon source.

STATE OF THE ART

Certain unicellular red algae (URA) can be of interest as an additional food source because they can be a source of proteins, for instance phycobiliproteins, fibre, lipids, or antioxidants, particularly carotenoids. They can be used in the native state, advantageously dried, but also processed, for example reduced to flour. They can be used non-therapeutically in human or animal diets as a nutritional supplement or can be incorporated in small amounts into food.

The red algae, or rhodophytes (division Rhodophyta), are a large taxon of mostly marine algae including both unicellular (URA) and multicellular organisms. The red algae are characterized by a pigmentary composition with chlorophyll "a", carotenoids and characteristic pigments, the phycobiliproteins.

URA are extremophilic organisms capable of tolerating very acidic pH (0.05-5) and very high temperatures (25-56° C.).

URA are cultivated on standard culture media and, depending on the culture method, can use as carbon source carbon dioxide gas or an organic carbon source such as sugars, organic acids or their salts, or alcohols or polyols. (Wolfgang Gross and Claus Schnarrenberger, 1995).

Certain documents cite lactose among numerous carbon sources for culturing microorganisms (WO 2014/074769), and notably for microalgae of the genus *Isochrysis* (WO 2012/175866). Tischendorf et al. (2007), in a study of plastids from *Galdieria*, a URA, describe its low-density culture in Erlenmeyer flasks in medium containing lactose. Lactose is also described among numerous sugars as antiflocculant for preventing the autoflocculation of freeze-dried microalgae (EP 2 730 647).

Apart from these examples, lactose is neither identified nor even used as carbon source in the industrial culture of microalgae. The cost of the raw material and the difficulty of arranging sufficient supplies at an economically viable price are part of the reason for this lack of use, whereas many less-expensive carbon sources are available in large amounts.

Lactose is a carbohydrate naturally present in mammalian milk. It is a disaccharide, the molecule being composed of glucose and galactose. It is the only milk carbohydrate. By way of example, cow's milk contains 5 g of lactose per 100 mL. Whey, obtained after separation of fats and precipitation of casein, is very lactose-rich, from 70% to 75% of the dry weight.

Milk permeate obtained after extraction of milk proteins by ultrafiltration can contain, after concentration by reverse osmosis to separate the water and after crystallization, up to roughly 86% lactose.

Whey permeate from the cheese industry has a composition similar to that of milk permeate, as does buttermilk from butter production.

Lacteal permeates in general, particularly that of milk, produced by the dairy industry are co-products which industrial producers have difficulty exploiting. The volumes of permeate produced by this industry are very large and it is not easy for industrial producers to find a market for this product or to use it, after concentration, crystallization of the lactose, and drying, as an expensive source of lactose added to the composition of certain reconstituted milks. Liquid permeates have no acceptable outlets and are poorly suited for culturing microorganisms capable of degrading them due to the presence of lactic acid and citric acid.

It is therefore understood that there exists a need for markets allowing value to be added to lacteal permeates whether milk permeate, whey permeate or buttermilk.

The inventors have shown that unicellular red algae (URA), advantageously of the class Cyanidiophyceae, are capable of growing in a medium containing a lacteal permeate as principal supply of at least one carbon source, said carbon source essentially containing lactose.

This invention makes it possible both to add value to a dairy industry waste product and to produce biomass rich in proteins and in high-added-value components such as pigments useful in the food industry.

DISCLOSURE OF THE INVENTION

The present invention relates to a method for producing unicellular red algae (URA) biomass, in particular URA of the class Cyanidiophyceae, comprising the following steps:

a) culturing said unicellular red algae (URA) in a medium containing at least one lacteal permeate comprising lactose as carbon source, lactate and citrate.

b) collecting from the culture medium the biomass produced containing said URA.

The expression "medium containing at least one lacteal permeate comprising lactose as carbon source", as used in the present text, refers to a medium for culturing microorganisms, in particular microalgae, of which all or part of the carbon source is in the form of lactose in an amount ranging between 0.05 g/L and 200 g/L, advantageously between 1 g/L and 150 g/L, very advantageously between 10 g/L and 80 g/L, said lactose coming from the lacteal permeate.

According to a particular embodiment of the invention, the culture method includes at least one illumination step.

The invention also relates to the biomass obtainable by this method.

DETAILED DESCRIPTION OF THE INVENTION

The first object of the present invention is a method for culturing unicellular red algae (URA), advantageously of the class Cyanidiophyceae, in a medium comprising lactose as carbon source in the form of lacteal permeate, in particular milk permeate, whey permeate or buttermilk, i.e., a culture medium containing at least one lacteal permeate comprising lactose as carbon source.

According to a first embodiment of the invention, lactose is the only carbon source in the culture medium. In this case the culture medium may include traces of other carbon matter degradable by URA, these traces coming from lactose or from other components added to the composition of the culture medium. Particular mention may be made of organic acids, such as lactic acid and citric acid, for example, contained in the lacteal permeate, which are also a carbon source.

The expression "lactose as the only carbon source in the culture medium" means that the culture medium does not contain carbon sources added to the lacteal permeate.

According to another embodiment of the invention, the culture medium can include another carbon source commonly used for culturing microorganisms, such as glucose, sucrose and acetate.

Preferentially, the elements contained in the lacteal permeates (lactose, organic acids, proteins) are the only carbon sources of the culture medium.

Further according to the invention, lactose can be at an initial concentration in the culture medium ranging between 0.05 g/L or even 0.1 g/L and 200 g/L, preferentially ranging between 1 g/L or even 5 g/L and 100 g/L, more preferentially 10 g/L and 30 g/L or even 80 g/L. The person skilled in the art, knowing the lactose content in the available lacteal permeate, will be able to determine the amount of permeate to be used in order to obtain the desired lactose concentration.

According to the invention, the term "lacteal permeate" refers to milk permeate, whey permeate or buttermilk, preferably milk permeate. These permeates generally contain from 80 to 250 g/L lactose.

According to the invention, any medium for culturing microalgae, particularly unicellular red algae (URA) of the class Cyanidiophyceae, described in the prior art can be adapted so that all or part of the carbon source contained therein is in the form of lactose, to be used in the method of the invention.

Hereinafter, for convenience and subject to clarification, the use of "URA" must be understood to mean "rhodophytes, in particular of the subdivision Cyanidiophytina, more particularly of the class Cyanidiophyceae, notably of the order Cyanidiales, of the family Cyanidiaceae or Galdieriaceae, advantageously of the genus *Cyanidioschyzon, Cyanidium* or *Galdieria*, of the species *Cyanidioschyzon merolae* 10D, *Cyanidioschyzon merolae* DBV201, *Cyanidium caldarium, Cyanidium daedalum, Cyanidum maximum, Cyanidium partitum, Cyanidium rumpens, Galdieria daedala, Galdieria maxima, Galdieria partita* or *Galdieria sulphuraria*".

Similarly, the use of the term "Cyanidiophyceae" must be understood, subject to clarification, as meaning "Cyanidiophyceae, of the order Cyanidiales, of the family Cyanidiaceae or Galdieriaceae, of the genus *Cyanidioschyzon, Cyanidium* or *Galdieria*, of the species *Cyanidioschyzon merolae* 10D, *Cyanidoschyzon merolae* DBV201, *Cyanidium caldarium, Cyanidium daedalum, Cyanidium maximum, Cyanidium partum, Cyanidum rumpens, Galderia daedala, Galdieria maxima, Galderia partita* or *Galdieria sulphuraria*"; the use of the term "Cyanidiales" must be understood, subject to clarification, as meaning "Cyanidiales, of the family Cyanidiaceae or Galdieriaceae, of the genus *Cyanidoschyzon, Cyanidium* or *Galdieria*, of the species *Cyanidioschyzon merolae* 10D, *Cyanidoschyzon merolae* DBV201, *Cyanidium caldarium, Cyanidium daedalum, Cyanidium maximum, Cyanidium partitum, Cyanidium rumpens, Galdieria daedala, Galdieria maxima, Galdieria partita* or *Galdieria sulphuraria*"; the use of the expression "Cyanidiaceae or Galdieriaceae" must be understood, subject to clarification, as meaning "Cyanidiaceae or Galdieriaceae, of the genus *Cyanidioschyzon, Cyanidium* or *Galderia*, of the species *Cyanidioschyzon merolae* 10D, *Cyanidioschyzon merolae* DBV201, *Cyanidium caldarium, Cyanidum daedalum, Cyanidum maximum, Cyanidium partitum, Cyanidium rumpens, Galderia daedala, Galdieria maxima, Galdieria partita* or *Galdieria sulphuraria*"; the use of the expression "*Cyanidoschyzon, Cyanidium* or *Galdieria*" must be understood, subject to clarification, as meaning "*Cyanidioschyzon, Cyanidium* or *Galdieria*, of the species *Cyanidioschyzon merolae* 10D, *Cyanidioschyzon merolae* DBV201, *Cyanidium caldarium, Cyanidum daedalum, Cyanidum maximum, Cyanidium partitum, Cyanidium rumpens, Galderia daedala, Galdieria maxima, Galdieria partita* or *Galderia sulphuraria*".

Preferably, the URA are selected from the family Cyanidiaceae or Galdieriaceae, particularly from the genus *Cyanidioschyzon, Cyanidium* or *Galdieria*, very particularly from the species *Cyanidioschyzon merolae* 10D, *Cyanidioschyzon merolae* DBV201, *Cyanidium caldarium, Cyanidium daedalum, Cyanidium maximum. Cyanidium partitum, Cyanidium rumpens, Galdieria daedala, Galdieria maxima, Galderia partita* or *Galdieria sulphuraria*, preferentially from the species *Galdieria sulphuraria*.

According to the invention, the culture can be carried out by any known culture technique, for example in flasks or in a reactor, but also in fermenters or in any container suited to URA growth such as, for example, raceways or open ponds, provided that said technique makes it possible to place the URA in contact with at least the carbon source comprising at least lactose, and if applicable equipped with at least one light source.

Another advantage of the method developed by the Applicant is that it can be performed in a bioreactor, advantageously on an industrial scale. Advantageously, the method of the invention is carried out in 1-$m^3$, 4-$m^3$, 10-$m^3$ and 200-$m^3$ bioreactors, or larger, which are the volumes commonly used in industrial production.

To the Applicant's knowledge, no industrial URA production (in a bioreactor) in a medium containing a lacteal permeate comprising lactose as carbon source is known.

Certain URA are mixotrophs, capable of both heterotrophy (consumption of organic carbon substrate provided by the culture medium) and autotrophy (use of light to capture $CO_2$ via photosynthesis). Mixotrophy is also called photoheterotrophy. The concept of mixotrophy extends to the use of light not only for photosynthesis but also as a light signal capable of inducing a metabolic response, for example synthesis of pigments.

Heterotroph-dominant mixotrophy allows the production of molecules of algal origin by coupling the advantages of both autotrophy and heterotrophy. It consists in introducing a light component of low intensity and short duration, with a culture medium which can contain one or more organic sources of carbon. As in heterotrophy, URA consume an organic substrate, which makes it possible to achieve high biomass productivity (expressed in grams of dry biomass/L/h) and/or biomass concentration (expressed in grams of dry biomass/L), wherein the chloroplast and other light-sensitive cell structures are thus activated.

These light-energy receptors can be specific organelles or structures within the cell, such as the chloroplast, the stigma, the chronoplast, the chromoplast or the phycobilisome, or can be individual molecules capable of responding to light and of producing a cellular response, such as the rhodopsins, the phytochromes, the cryptochromes or the aureochromes.

These photoreceptors enable the cell to have higher productivity and to synthesize all the molecules metabolizable by a URA. The molecules of interest produced by said URA are of major industrial interest particularly in the fields of nutrition, cosmetics, green chemistry and energy.

These molecules of interest are varied and include, for example, carbohydrates, proteins, amino acids, advantageously essential amino acids and pigments, particularly photosynthetic pigments, the main ones being chlorophylls, carotenoids and phycobiliproteins.

The Applicant has also shown, surprisingly and after extensive research, that culturing URA in a culture medium containing at least one lacteal permeate comprising lactose as carbon source and at least one illumination step, advantageously illumination by light having a narrow spectrum centred over a given wavelength, particularly a spectrum centred at 455 nm, can make it possible to obtain biomass in which the amount in URA can be substantially increased relative to the cultures typically produced and which, moreover, can contain a potentially higher amount of molecules of interest, particularly phycobiliproteins, particularly phycocyanin, allophycocyanin, phycoerythrin, zeaxanthin and β-carotenes, than that which can be obtained in the cultures of the prior art.

Therefore, the invention also relates to a method for culturing unicellular red algae (URA), advantageously of the class Cyanidiophyceae, in a medium containing at least one lacteal permeate comprising lactose as carbon source, said method comprising at least one illumination step. This method makes it possible to obtain a biomass productivity and/or concentration which is substantially increased relative to the cultures typically produced, biomass which in addition can be advantageously rich in phycocyanin and/or carotenoids.

The expression "rich in phycocyanin and/or carotenoids" as used herein means that the concentration of phycobiliproteins and/or of carotenoids in the biomass which can be produced after culture under the conditions of the invention is higher than the concentration of phycobiliproteins and/or of carotenoids which can be produced by biomass of the same algae obtained after culture under the conditions of the prior art.

The biomass obtained advantageously includes intracellular contents of phycobiliproteins (mainly phycocyanin and allophycocyanin) ranging between 29 and 250 mg/g dry matter, preferentially between 35 and 150 mg/g dry matter and potentially rich in antioxidants, in particular in carotenoids, advantageously zeaxanthin and β-carotene, in contents ranging between 0.1 and 10 mg/g, advantageously between 0.250 and 1 mg/g.

According to the invention, the illumination step of the method can be performed using white light or, advantageously, blue light or violet light. Preferentially, according to a variant of the invention, the illumination step of the method can be performed using blue light.

According to the invention, blue light refers to radiation having a narrow wavelength spectrum between 400 and 550 nm, preferentially between 420 nm and 500 nm. Such radiation can make it possible to obtain biomass rich in phycocyanin and in antioxidants, particularly carotenoids. According to a variant of the invention, said spectrum can be centred at 455 nm and not extend beyond 25 nm on each side. Preferably, according to the invention, the selected wavelength will be between 430 and 480 nm, more preferentially the selected wavelength will be 455 nm.

According to the invention, the illumination can be produced by any means known to those skilled in the art, notably one or more lamps, one or more tubes, one or more light-emitting diodes (LEDs).

The Applicant has shown that the method is even more effective when the illumination is produced by one or more light-emitting diodes (LEDs). Thus, according to a variant of the invention, the illumination can be produced by one or more LEDs. The LEDs are preferably commercially available LEDs. By way of example, mention may be made of LEDs from Seoul Optodevice Co., LTD (South Korea), from Nichia Corporation (Japan), or from SunLED Corporation (USA).

According to the method of the invention, the culture can be subjected to light radiation for a sufficient period corresponding at least to the period necessary to meet the desired criteria of growth rate, phycocyanin level and/or carotenoid level. Those skilled in the art will be able, without excessive experimentation, to determine this required period. They will be able to adapt this time based on their knowledge of the field.

More particularly, mixotrophic conditions can be obtained under illumination conditions that are discontinuous and/or variable over time.

Discontinuous illumination refers to illumination punctuated by periods of darkness. In particular, the illumination can be in the form of flashes. A flash, within the meaning of the invention, is light illumination of given duration.

According to the invention, three illumination concepts must be considered: the frequency or the number of flashes per unit of time, the duration of the flash, and the intensity of the light emitted.

In terms of frequency, according to the invention, depending on the number of flashes per unit of time used in the method of the invention, two types of illumination are defined:
  a low-frequency illumination wherein the number of flashes can be between about 2 and $3.6 \times 10^4$ per hour ($5.4 \times 10^{-4}$ Hz to 10 Hz), preferentially between 3 and $3.6 \times 10^3$ per hour ($8.3 \times 10^{-4}$ Hz to 1 Hz). It is understood here that the number of flashes per hour may have all the values between 2 and 36000 without it being necessary to mention them all (2, 3, 4, . . . , 35598, 35599, 36000);
  a high-frequency illumination wherein the number of flashes can be between about $3.6 \times 10^4$ and $5.4 \times 10^9$ (10 Hz to $1.5 \times 10^6$ Hz) per hour, preferentially between $3.6 \times 10^5$ and $5.4 \times 10^9$ (100 Hz to $1.5 \times 10^6$ Hz). It is understood here that the number of flashes per hour may have all the values between $3.6 \times 10^5$ and $5.4 \times 10^9$ without it being necessary to mention them all (36000, 36001, 36002, . . . , 5399999998, 5399999999, 5400000000).

In terms of duration according to the invention, irrespective of the chosen illumination frequency, the flash duration can be between $1/150000$ of a second and 1799 seconds (29 minutes and 59 seconds).

Of course, when high-frequency illumination is used, the flash duration can be preferentially between $1/150000$ of a second and $1/10$ of a second.

And when low-frequency illumination is used, the flash duration can be preferentially between $1/10$ of a second and 1799 seconds (29 minutes and 59 seconds).

In terms of light intensity according to the invention, the intensity of the light provided in the form of flashes can be between 5 and 5000 µmol·m$^{-2}$·s$^{-1}$, preferably between 5 and 500 µmol·m$^{-2}$·s$^{-1}$, or 50 and 400 µmol·m$^{-2}$·s$^{-1}$, and more preferentially between 150 and 300 µmol·m$^{-2}$·s$^{-1}$ (1 µmol·m$^{-2}$·s$^{-1}$ corresponds to 1 µE m$^{-2}$·s$^{-1}$ (einstein), a unit often used in the literature).

According to the invention, the number of flashes per hour can be selected as a function of the intensity and the duration of the flashes (see above).

According to the invention, the concepts of frequency, duration and light intensity apply to the illumination as envisaged by the invention, i.e., the illumination produced by the chosen light source, advantageously by an LED, emitting light radiation having a narrow spectrum between 400 and 550 nm, preferably 420 and 500 nm, even more preferentially between 430 and 480 nm, more preferentially centred at 455 nm and for the periods considered according to the invention.

A preferred form of the invention can be a method of the invention in which the illumination can be provided in the form of discontinuous light in the form of flashes, obtained with LEDs emitting radiation having a narrow wavelength spectrum between 400 nm and 550 nm, preferentially between 420 nm and 500 nm, more preferentially between 430 and 480 nm, most preferentially a wavelength of 455 nm.

According to another embodiment of the invention, the illumination can be variable, which means that the illumination is not interrupted by phases of darkness, but that the light intensity varies over time. This variation of light intensity can be regular or irregular and can be periodic or cyclic. According to the invention, light may also be provided in a combination of continuous and discontinuous illumination phases.

Variable illumination means that the light intensity varies in a regular manner at least twice per hour.

Such culture means and methods with variable or flash illumination are described in application WO 2012/035262.

The illumination may have, preferably, variations of intensity having an amplitude generally between 5 µmol·m$^{-2}$·s$^{-1}$ and 5000 µmol·m$^{-2}$·s$^{-1}$, preferably between 50 and 1500 µmol·m$^{-2}$·s$^{-1}$, more preferentially between 50 and 200 µmol·m$^{-2}$·s$^{-1}$.

According to a preferred embodiment, the illumination has variations of intensity having an amplitude between 5 and 1000 µmol·m$^{-2}$·s$^{-1}$, preferably between 5 and 400 µmol·m$^{-2}$·s$^{-1}$, these variations taking place between 2 and 3600 times per hour, preferably between 2 and 200 times per hour.

These culture conditions make it possible to provide a defined quantity of light. This light provision may comprise discontinuous and/or variable illumination phases, with variations of intensity that may have identical or different amplitudes.

According to the invention, the culture conditions for the URA strains can be the conditions known and used in the prior art to cultivate the selected strains, conditions to which an illumination step has been added. This illumination step can be added at the beginning, in the middle or at the end of culture, the method therefore being a combination of heterotrophic culture and of mixotrophic culture.

According to a particular embodiment of the invention, culture step a1) includes a first heterotrophic culture step, followed by a mixotrophic culture step a2) until the end of the culture before proceeding to biomass collection step b).

According to another embodiment of the invention, all of culture step a) is carried out in mixotrophic mode, the illumination conditions which can be constant or variable over time.

Advantageously, the conditions which will make it possible to obtain the best biomass productivity and/or the best biomass concentration will be used.

Those skilled in the art will be able to integrate the illumination step according to the invention in a known method, in order to obtain biomass that meets the desired criteria according to the invention in terms of growth rate and levels of metabolites of interest, particularly in levels of carotenoids and/or phycobiliproteins. In this respect, mention may be made of the methods described by Wolfgang Gross and Claus Schnarrenberger (op. cit.).

The methods for obtaining high biomass productivity or biomass concentration can be favoured. As an exemplary method, mention may be made of that described for example by Graverholt et al. (2007).

More particularly, this step can be integrated in the methods described in application WO 2012/035262.

Generally according to the invention, the culture according to the method may be carried out at a temperature ranging between 15° C. and 47° C., advantageously between 22° C. and 42° C.

According to the invention, the culture method can be used to cultivate a single URA strain of a given genus, several strains of a single given genus, or several strains of different given genera (at least two species of two different genera).

The organic carbon substrate, other than lactose, contained if necessary in the culture medium may consist of complex molecules or a mixture of substrates. Products derived from the biotransformation of starch, for example from maize, wheat or potato, notably starch hydrolysates, which consist of small molecules, constitute, for example, organic carbon substrates suited to mixotrophic culture of the cells according to the invention.

The amounts of carbon sources used according to the method will of course depend on the chosen strain. Here again, those skilled in the art will easily know how to adapt the amounts of carbon source to the strain to be cultivated in pure form or in mixture.

According to an embodiment of the invention, the total carbon source, whether lactose alone or lactose and at least one other carbon source, may have a concentration ranging between 0.05 g/L and 200 g/L, preferably 0.5 g/L and 100 g/L.

The method of the invention can further comprise a step of collecting the URA. Said collection of the URA can be performed by any technique enabling collection of the biomass, in particular gravimetric or low-pressure filtration methods, decantation methods, or even precipitation methods followed by gravimetric filtration.

The invention also relates to the biomass obtainable by any one of the variants of the method of the invention.

The term "biomass" according to the invention advantageously refers to a collection of microorganism cells produced by culture thereof, cells which may or may not have retained their physical integrity. It is therefore understood that said biomass can include a quantity of degraded microorganism cells ranging from 0% to 100%. The term "degraded" means that the physical integrity of said microorganism cells may be deteriorated, such as for example lysed microorganisms, resulting for example from a process of homogenization or of enzymatic lysis. Once produced, this biomass may be crude, just separated from its culture medium, dried or not, degraded or not.

The biomass, depending on whether it is completely or partially dried or not, can comprise a water content of 1% to 90%.

According to a first embodiment, the biomass has a water content of 70% to 90%, preferentially 80% to 85%. It is in particular the case when it essentially consists of optimized and cultivated industrial microorganisms, after filtration of the fermentation must in order to separate the cultivated microorganisms from the culture medium, before drying.

According to another embodiment of the invention, the biomass is completely or partially dried and has a water content of 1% to 10%, preferentially of 2% to 7%. According to the invention, said biomass can have a URA density ranging between 20 and 200 g/L dry matter, preferentially between 90 and 150 g/L dry matter.

According to the invention, said biomass can have a protein content ranging between 25% and 60%, even up to 70%, preferably between 30% and 55%, more preferentially between 40% and 50% of the dry weight. The determination of nitrogen content and the calculation of 10 crude protein content are performed according to the method using block digestion and steam distillation (NF EN ISO 5983-2).

According to the invention, said biomass can have an intracellular phycobiliprotein content (phycocyanin and allophycocyanin) ranging between 1 and 250 mg/g dry matter, preferentially between 20 and 150 mg/g dry matter.

Further according to the invention, said biomass can have an intracellular phycocyanin content ranging between 0.5 and 100 mg/g dry matter, preferentially between 10 and 40 mg/g dry matter.

The biomass may be packaged for storage or for use as such, for example as food supplement or as food for human or animal consumption.

The meal obtainable after extracting phycocyanin from the URA biomass obtainable by the method of the invention can be used as a protein and carotenoid-rich food supplement in food for human or animal consumption.

According to the invention, said biomass can have an intracellular carotenoid content ranging between 0.1 and 10 mg/g dry matter, advantageously between 0.250 and 1 mg/g dry matter.

URA have a high potential for use in many fields, such as food for human or animal consumption, cosmetics, medicine, for example.

According to the invention, said URA biomass obtainable according to the invention can be used after harvest either directly, optionally dried, or after processing. In particular, said biomass can be used in the form of flours included in food compositions or in the form of food supplements.

The URA biomass obtainable according to the invention can be processed into flour according to any method known to those skilled in the art. It can thus be envisaged, for example, that the URA can be separated from the culture medium, lysed and reduced to fine particles (average diameter of 10 microns), then dried.

The invention also relates to any use of the URA biomass obtainable according to the invention in any known field of use of URA, particularly food for human or animal consumption, cosmetics, medicine. In the fields of food for human or animal consumption and of cosmetics, it is obviously a matter of non-therapeutic uses intended for healthy animals or humans.

The biomass obtained after culturing URA according to the method of the invention can make it possible to obtain in particular a flour that is rich in antioxidants, in particular in carotenoids (particularly zeaxanthin and β-carotenes) in amounts between 0.1 and 10 mg/g dry matter, advantageously between 0.25 and 1 mg/g dry matter, in particular including zeaxanthin in an amount between 0.05 and 5 mg/g dry matter, advantageously between 0.1 and 1 mg/g dry matter, and/or β-carotene in an amount 0.05 and 5 mg/g dry matter, advantageously between 0.1 and 1 mg/g dry matter, meeting a need particularly in the food industry by virtue of being more appetizing, having better taste, providing antioxidants in a large amount and being usable in food for human or animal consumption.

The invention thus relates to a flour obtainable after processing of the URA biomass obtainable by the method of the invention.

Irrespective of the form of use of the product obtainable by the method of the invention (native or processed biomass), said product can be used pure or mixed with other ingredients conventionally used, particularly in non-therapeutic uses in food or in cosmetics.

The invention also relates to any product that may comprise at least the algae biomass obtainable according to the invention. The invention also relates to any product that may comprise at least the flour derived from the processing of the algae biomass obtainable according to the invention.

Under mixotrophic conditions, culture of *Galdieria* on milk permeate as lactose source takes a yellow-white colour and loses its blue-green pigmentation. Several studies have shown that several key steps of the synthetic pathway of phycocyanin and of chlorophyll are induced by light and others suppressed in the presence of organic substrates, such as glucose, in the medium (Stadnichuck et al., 1998). On milk permeate the inhibitory effect of lactose is even more pronounced and leads to a total loss of chlorophyll and phycocyanin. However, there exist natural mutants (Gross et al., 1995; Sloth et al. 2006) capable of producing phycocyanin even under heterotrophic conditions on glucose. It can therefore be envisaged to use such a strain to produce phycocyanin under heterotrophic conditions or under mixotrophic conditions, and lactose as main carbon source.

According to the invention, phycobiliproteins, and particularly phycocyanin, produced by said biomass can be extracted for use, for example, in food or as colourant. Extraction of phycobiliproteins, and particularly of phycocyanin, from said biomass can be done according to any extraction technique known to persons skilled in the art, such as, for example, that described by Moon et al. (2014) or by Jaouen et al. (1999) or in application FR 2 789 399.

The invention also relates to the use of phycocyanin obtainable according to the method of the invention, in food for human or animal consumption, as food supplement, or as colourant, particularly as food colouring.

It will be noted that in the present text, as they may be used in the description and the claims, the singular forms "a" and 'an' also refer to their plurals, except if the context clearly states otherwise.

Figure 1A:
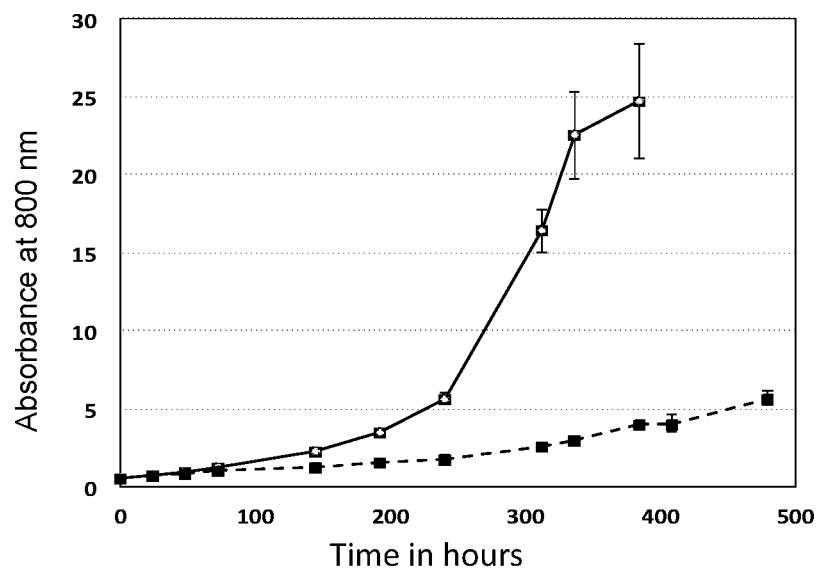
FIGS. 1A, 1B and 1C depicts the growth of strain *Galdieria sulphuraria* UTEX 2919 on milk permeate in Erlenmeyer flasks.
Figure 1B:
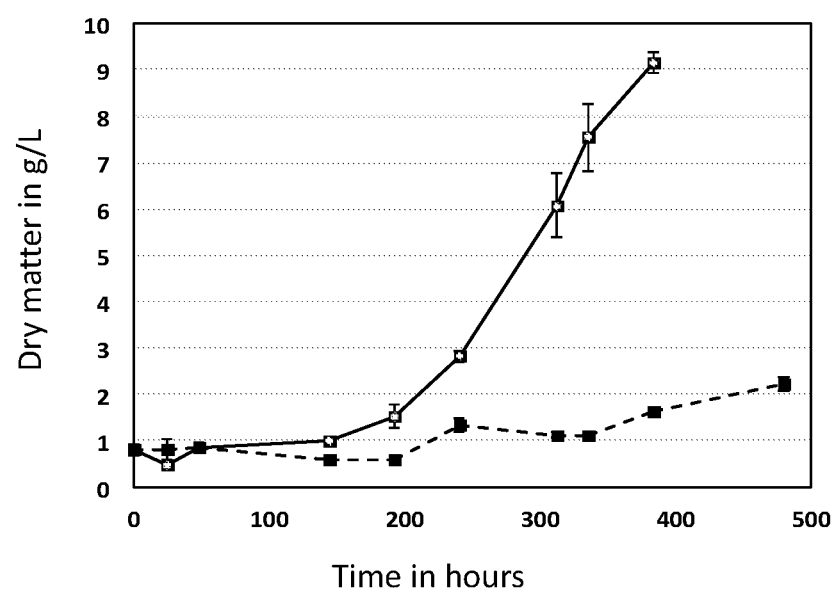
Figure 1C:
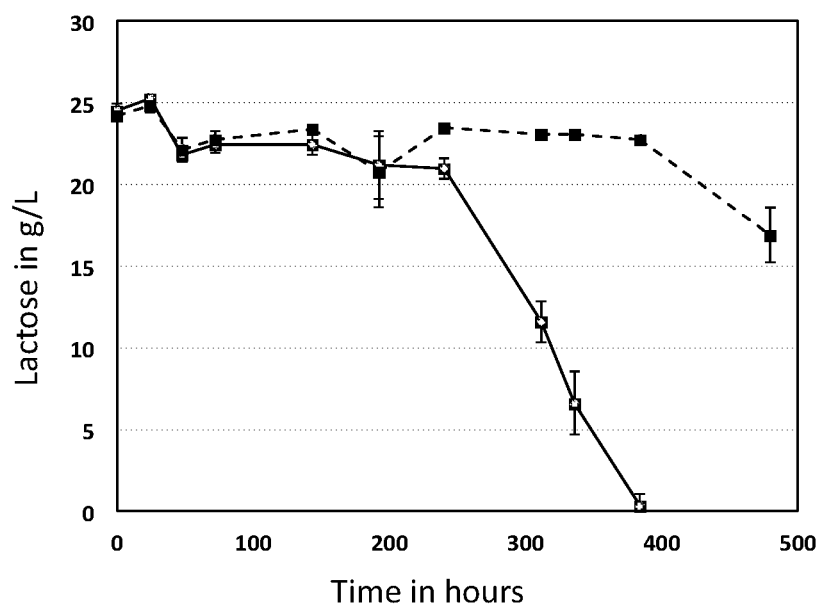

Other features and advantages of the invention will become apparent by reading the following examples, which illustrate but do not limit the present application, as well as the appended figures wherein:

FIG. 1A depicts the growth of strain *Galdieria sulphuraria* UTEX 2919 on milk permeate in Erlenmeyer flasks, with in (A) monitoring of growth by absorbance at 800 nm over time. FIG. 1B depicts the growth of strain *Galdieria sulphuraria* UTEX 2919 on milk permeate in Erlenmeyer flasks, with monitoring of growth by dry weight over time. FIG. 1C depicts the growth of strain *Galdieria sulphuraria* UTEX 2919 on milk permeate in Erlenmeyer flasks, with monitoring of consumption of lactose in the medium measured over time. The lactose concentration of the medium is measured by HPLC. Each curve ( -O-) representing growth of the strain under mixotrophic conditions, and ( --■--) representing growth of the strain under heterotrophic conditions, is an average of three tests.

Figure 2:
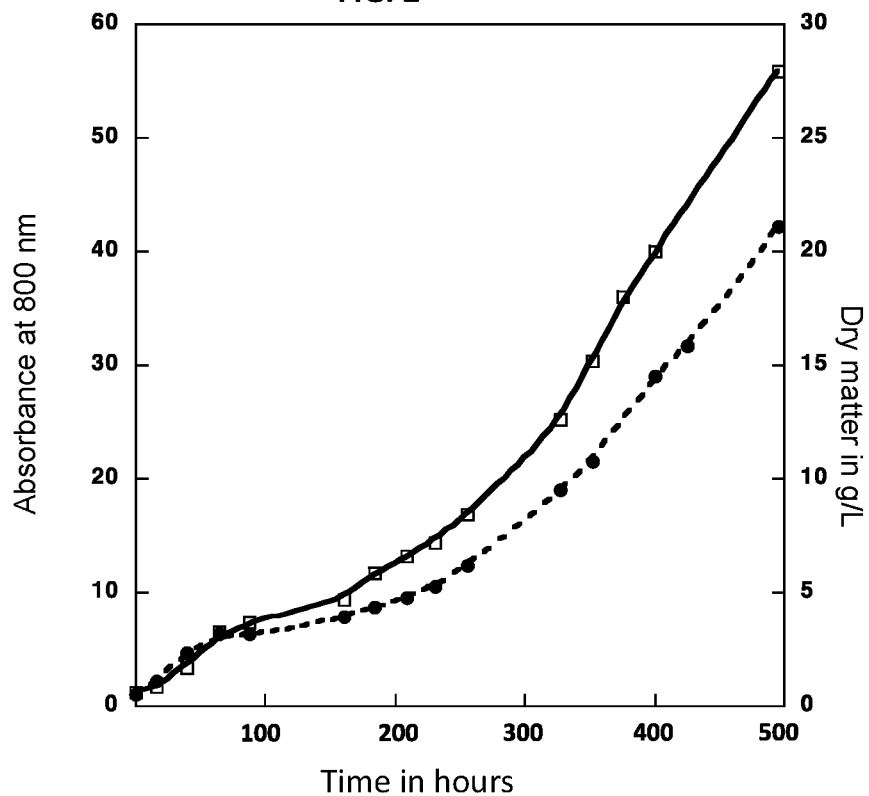
FIG. 2 depicts the growth of strain *Galdieria sulphuraria* UTEX 2919 on rehydrated powdered milk permeate in a fermenter.

FIG. 2 depicts the growth of strain *Galdieria sulphuraria* UTEX 2919 on rehydrated powdered milk permeate in a fermenter; ( -□-) monitoring of growth by absorbance at 800 nm over time; ( --●--) monitoring of growth by dry weight over time.

Figure 3:
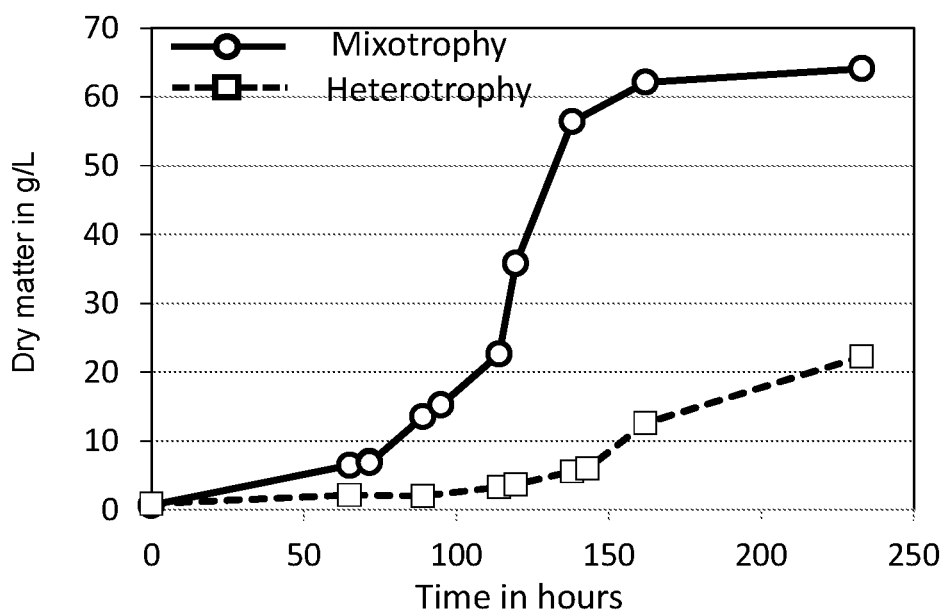
FIG. 3 depicts the growth of strain *Galdieria sulphuraria* UTEX 2919 on liquid milk permeate in a fermenter.

FIG. 3 depicts the growth of strain *Galdieria sulphuraria* UTEX 2919 on liquid milk permeate in a fermenter; ( --⌐--) monitoring of growth under heterotrophic conditions by dry weight overtime; ( -O-) monitoring of growth under mixotrophic conditions by dry weight over time.

EXAMPLES

Example 1: Monitoring of Growth of Strain *Galdieria sulphuraria* on Milk Permeate in Erlenmeyer Flasks Growth of the strain is monitored by absorbance at 800 nm overtime. The culture medium is a conventional medium for this strain, except that the medium comprises 30 g/L milk permeate, which corresponds to about 25 g/L lactose.

Materials and Methods

Strain: *Galdieria sulphuraria* (also called *Cyanidum caldarium*) UTEX #2919

Culture Medium:

30 g/L milk permeate (roughly 25 g/L lactose), 8 g/L $(NH_4)_2SO_4$, 1 g/L $KH_2PO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4·5H_2O$; 2.860 g/L $H_3BO_3$; 0.040 g/L $NaVO_3·4H_2O$; 1.820 g/L $MnCl_2$; 0.040 g/L $CoCl_2·6H_2O$; 0.220 g/L $ZnSO_4·7H_2O$; 0.017 g/L $Na_2SeO_3$; 0.030 g/L $(NH_4)_6Mo_7O_{24}·4H_2O$).

Culture Conditions:

The culture is carried out on a shaker table (140 rpm) in a temperature-controlled enclosure (37° C.), in medium as described above in the presence of a light source. The culture time was between 200 and 500 hours.

Culture Monitoring:

Growth is monitored by measurement of absorbance at 800 nm with a spectrophotometer. Total biomass concentration is monitored by measurement of dry weight (filtration on a Whatman GF/F filter and then drying in a 105° C. oven for at least 24 hours before weighing).

The results are presented in FIGS. 1A, 1B and 1C.

Results

Growth monitoring shows that high OD values are reached and that all lactose was consumed. The determination of lactose content was performed by HPLC (Shimatsu) in isocratic mode (5 mM $H_2SO_4$) and refractive index (RI) detection. During these HPLC analyses no trace of glucose or galactose, synonymous with lactose hydrolysis, could be detected in the medium.

Results of analyses of the amino acid content of the strain are described in Tables 1A, 1B and 1C below:

TABLE 1(A)

Amino acid content of the strain having grown on lactose under mixotrophic conditions. Amount of amino acids expressed for 100 g dry weight.

| 1A | | | | | | | | |
|---|---|---|---|---|---|---|---|---|
| ASP | GLU | ALA | ARG | CYS* | GLY | HIS | ILE | LEU |
| 3.73 | 7.16 | 2.37 | 2.5 | 1.04 | 2.00 | 0.958 | 2.21 | 3.5 |
| LYS | MET | PHE | PRO | SER | THR | TYR | VAL | TRP |
| 3.25 | 1.04 | 2.06 | 2.31 | 3.06 | 2.74 | 2.85 | 2.97 | 0.72 |
| TOTAL: 46.47 | | | | | | | | |

*Cysteine + Cystine; Values given in g/100 g dry weight

TABLE 1(B)

Amino acid content of the strain having grown on lactose under mixotrophic conditions: Amino acid scores comparing FAO recommended daily requirements and the amounts provided by the strains of this study (mg/g of proteins).

| 1B | mg/g N*6.25 (FAO) | mg/g N*6.25 UTEX 2919 |
|---|---|---|
| HIS | 16 | 18.66 |
| ILE | 30 | 43.04 |
| LEU | 61 | 68.16 |
| LYS | 48 | 63.29 |
| MET + CYS | 23 | 40.51 |
| PHE + TYR | 41 | 95.62 |
| THR | 25 | 53.36 |
| TRP | 6.6 | 14.02 |
| VAL | 40 | 57.84 |

TABLE 1(C)

Amino acid content of the strain having grown on lactose under mixotrophic conditions: Estimate of amount of proteins (N*6.25) by measurement of total nitrogen.

| 1C | Total N | N*6.25 |
|---|---|---|
| Kjeldahl | 8.217 | 51.35 |

The protein content, estimated by the Kjeldahl method, was estimated at 51.35% using the factor N*6.25.

The daily supply of essential amino acids provided by the consumption of 100 g of *Galdieria sulphuraria* proteins, produced under the conditions described above, is higher than the FAO recommendations.

Example 2: Monitoring of Growth of Strain *Galdieria sulphuraria* on Rehydrated Powdered Milk Permeate in a Fermenter Growth of the strain is monitored by measurement of absorbance at 800 nm over time. The culture medium is a conventional medium for this strain, except that the medium comprises 30 g/L milk permeate, which corresponds to about 25 g/L lactose, 3.12 g/L citrate, and 0.76 g/L lactate.

Materials and Methods

Strain: *Galdieria sulphuraria* (also called *Cyanidum caldarium*) UTEX #2919

Culture Medium:

30 g/L milk permeate (roughly 25 g/L lactose, 3.12 g/L citrate, and 0.76 g/L lactate), 8 g/L $(NH_4)_2SO_4$, 1 g/L $KH_2PO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4 \cdot 5H_2O$; 2.860 g/L $H_3BO_3$; 0.040 g/L $NaVO_3 \cdot 4H_2O$; 1.820 g/L $MnCl_2$; 0.040 g/L $CoCl_2 \cdot 6H_2O$; 0.220 g/L $ZnSO_4 \cdot 7H_2O$; 0.017 g/L $Na_2SeO_3$; 0.030 g/L $(NH_4)_6Mo_7O_{24} \cdot 4H_2O$).

Culture Conditions:

The cultures are carried out in 1- to 2-L-useful-volume reactors with computer-controlled automated systems. Culture pH is controlled by adding base (14% ammonia solution (wNH$_3$/w) and/or acid (4 N sulphuric acid solution). Culture temperature is set to 42° C. Agitation is provided by three impellers: one Rushton turbine with six straight blades positioned at the lower end of the agitator shaft above the sparger and two triple-bladed HTPG2 impellers placed on the agitator shaft. Dissolved oxygen pressure in the liquid phase is regulated in the medium throughout the culture by the rotational speed of the agitator shaft (250-1800 rpm) and the air and/or oxygen ventilation flow rate. The regulatory parameters, integrated into the computer-controlled automated system, make it possible to maintain a partial pressure of dissolved oxygen in the liquid phase between 5 and 30% of the air saturation value under identical conditions of temperature, pressure and medium composition. Culture time was between 200 and 500 hours. Additions of nutrient solution containing 100 g/L milk permeate are carried out overtime in order to maintain a lactose concentration in the fermenter ranging between 10 and 20 g/L.

Growth is monitored by measurement of absorbance at 800 nm with a spectrophotometer. Total biomass concentration is monitored by measurement of dry weight (filtration on a Whatman GF/F filter and then drying in a 105° C. oven for at least 24 hours before weighing).

The results of this test are presented in FIG. 2.

Results

Growth monitoring shows that high OD values and a dry weight of more than 20 grams per litre of culture are reached, with lactose as the only carbon source.

Example 3: Monitoring of Growth of Strain *Galdieria sulphuraria* on Liquid Milk Permeate in a Fermenter Growth of the strain is monitored by measurement of absorbance at 800 nm over time. The culture medium is a conventional medium for this strain, except that the medium comprises liquid milk permeate containing about 81 g/L lactose, 11.9 g/L citrate, 2.8 g/L lactate.

Materials and Methods

Strain: *Galdieria sulphuraria* (also called *Cyanidum caldarium*) UTEX #2919

Culture Medium:

Milk permeate (roughly 25 g/L lactose, 3.65 g/L citrate, and 0.86 g/L lactate), 8 g/L $(NH_4)_2SO_4$, 1 g/L $KH_2PO_4$, 716 mg/L $MgSO_4$, 44 mg/L $CaCl_2$, 3 mL/L Fe-EDTA stock solution (6.9 g/L $FeSO_4$ and 9.3 g/L EDTA-$Na_2$) and 4 mL/L trace metal solution (3.09 g/L EDTA-$Na_2$; 0.080 g/L $CuSO_4 \cdot 5H_2O$; 2.860 g/L $H_3BO_3$; 0.040 g/L $NaVO_3 \cdot 4H_2O$; 1.820 g/L $MnCl_2$; 0.040 g/L $CoCl_2 \cdot 6H_2O$; 0.220 g/L $ZnSO_4 \cdot 7H_2O$; 0.017 g/L $Na_2SeO_3$; 0.030 g/L $(NH_4)_6Mo_7O_{24} \cdot 4H_2O$).

Culture Conditions:

The cultures are carried out in 1- to 2-L-useful-volume reactors with computer-controlled automated systems. Culture pH is controlled by adding base (14% ammonia solution (wNH$_3$/w) and/or acid (4 N sulphuric acid solution). Culture temperature is set to 42° C. Agitation is provided by three impellers: one Rushton turbine with six straight blades positioned at the lower end of the agitator shaft above the sparger and two triple-bladed HTPG2 impellers placed on the agitator shaft. Dissolved oxygen pressure in the liquid phase is regulated in the medium throughout the culture by the rotational speed of the agitator shaft (250-1800 rpm) and the air and/or oxygen ventilation flow rate. The regulatory parameters, integrated into the computer-controlled automated system, make it possible to maintain a partial pressure of dissolved oxygen in the liquid phase between 5 and 30% of the air saturation value under identical conditions of temperature, pressure and medium composition. Culture time was between 200 and 250 hours. Additions of nutrient solution containing 81 g/L milk permeate are carried out overtime in order to maintain a lactose concentration in the fermenter ranging between 10 and 20 g/L Under mixotrophic conditions, the cells are illuminated by a system of light baffles equipped with an LED system, delivering continuous white light with a power of 3 watts.

Growth is monitored by measurement of absorbance at 800 nm with a spectrophotometer. Total biomass concentration is monitored by measurement of dry weight (filtration on a Whatman GF/F filter and then drying in a 105° C. oven for at least 24 hours before weighing).

Results

The results of this test are presented in FIG. 3.

The growth measurements clearly show that growth on permeate under mixotrophic conditions is higher than under heterotrophic conditions. This also translates into much higher average rates of consumption of organic substrates contained in the medium (Tables 2A and 2B). The results presented in this table also show that strain UTEX 2919 is capable of consuming organic acids, such as citric acid and lactic acid, contained in the milk permeate in substantial proportions.

TABLE 2(A)

Consumption of organic substrates contained in the milk permeate, under mixotrophic conditions. UTEX 2919 Mixotrophy on Milk Permeate

|  | Total amount added (g) | Average consumption in g/L/h | Percentage consumed (%) |
|---|---|---|---|
| Lactose | 94 | 0.27 | 100 |
| Lactate | 3.4 | 0.009 | 98 |
| Citrate | 14.4 | 0.032 | 79 |

TABLE 2B

Consumption of organic substrates contained in the milk permeate, under heterotrophic conditions. UTEX 2919 Heterotrophy on Milk Permeate

|  | Total amount added (g) | Average consumption in g/L/h | Percentage consumed (%) |
|---|---|---|---|
| Lactose | 34 | 0.17 | 100 |
| Lactate | 1.6 | 0.004 | 58 |
| Citrate | 4.5 | 0.009 | 42 |

Under mixotrophic conditions, all lactose is consumed at the end of growth, as well as 98% and 80% of the citrate; the rates of consumption of the substrates are between 1.5 and 3.5 times faster.

REFERENCES

Graverholt et al. (2007), Appl. Microbiol. Biotechnol. (2007) 77:69-75
Gross et al., (1995), Plant and Cell Physiology 36, no. 4 (Jun. 1, 1995): 633-38
Jaouen et al., (1999), Biotechnology Techniques 13, no. 12 (December 1999): 877-81
Moon et al., (2014), "Isolation and Characterization of Thermostable Phycocyanin from *Galdieria Sulphuraria*" 31 (2014): 1-6
Sloth et al., (2006), Enzyme and Microbial Technology 38, no. 1-2 (Jan. 3, 2006): 168-75
Stadnichuck et al., (1998) Plant Science 136, no. 1 (Aug. 7, 1998): 11-23
Tischendorf et al. (2007), European Journal of Phycology, vol. 42, no. 3, 1 Aug. 2007, 243-251
EP 2 730 647
FR 2 789 399
WO 2012/035262
WO 2014/074769
WO 2012/175866

The invention claimed is:

1. A method for obtaining a flour comprising unicellular red algae (URA) biomass, said URA being selected from the genus *Galdieria*, the method comprising:
   a) cultivating URA in a medium containing at least one lacteal permeate selected from milk permeate, whey permeate, buttermilk and mixtures thereof; the lacteal permeate comprising lactose as carbon source and organic acids selected from lactic acid and citric acid;
   b) collecting the URA biomass from the medium of step a); and
   c) processing the collected URA biomass into a flour;
wherein the lactose from lacteal permeate is at an initial concentration in the culture medium ranging between about 0.05 g/L and about 200 g/L; and the URA biomass produced has a URA density of between 20 and 200 g/L dry matter.

2. The method of claim 1, wherein the lactose is at an initial concentration in the medium ranging between about 0.1 g/L and about 150 g/L.

3. The method of claim 1, wherein the lactose is at an initial concentration in the medium ranging between about 10 g/L and about 80 g/L.

4. The method of claim 1, wherein the total carbon source is at an initial concentration in the medium of between about 0.05 g/L and about 200 g/L.

5. The method of claim 1, wherein the total carbon source is at an initial concentration in the medium of between about 0.5 g/L and about 100 g/L.

6. The method of claim 1, wherein the flour has an average particle diameter of 10 microns.

7. The method of claim 1, wherein lactose is the only carbon source in the medium.

8. The method of claim 1, wherein the medium includes lactose from the lacteal permeate and an additional carbon source.

9. The method of claim 8, wherein the additional carbon source other that lactose is glucose, sucrose, or acetate, or a combination thereof.

10. The method of claim 1, further including at least one illumination step.

11. The method of claim 1, wherein the URA is *Galdieria daedala, Galdieria maxima, Galdieria partita* or *Galdieria sulphuraria*.

12. The method of claim 1, wherein the URA is of the species *Galdieria sulphuraria*.

13. The method of claim 1, wherein the lacteal permeate is milk permeate.

14. A method for obtaining a food supplement comprising unicellular red algae (URA) biomass, said URA being selected from the genus *Galdieria*, the method comprising adding the flour of claim 1 into a food supplement.

15. The method of claim 14, wherein the food supplement is for human consumption.

16. The method of claim 14, wherein the food supplement is for animal consumption.

* * * * *